(12) United States Patent
Claus et al.

(10) Patent No.: US 9,468,409 B2
(45) Date of Patent: Oct. 18, 2016

(54) SYSTEMS AND METHODS FOR IMAGING DYNAMIC PROCESSES

(71) Applicant: General Electric Company, Schenectady, NY (US)

(72) Inventors: Bernhard Erich Hermann Claus, Niskayuna, NY (US); Jeffrey Wayne Eberhard, Albany, NY (US); David Allen Langan, Clifton Park, NY (US); Kedar Bhalchandra Khare, New Delhi (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 248 days.

(21) Appl. No.: 14/090,677

(22) Filed: Nov. 26, 2013

(65) Prior Publication Data
US 2014/0153690 A1  Jun. 5, 2014

(30) Foreign Application Priority Data
Nov. 30, 2012 (IN) .......................... 5013/CHE/2012

(51) Int. Cl.
*A61B 6/03* (2006.01)
*A61B 6/02* (2006.01)
*A61B 6/00* (2006.01)

(52) U.S. Cl.
CPC ............. *A61B 6/025* (2013.01); *A61B 6/027* (2013.01); *A61B 6/4441* (2013.01); *A61B 6/542* (2013.01)

(58) Field of Classification Search
USPC ...................................... 378/4, 21, 38, 9, 12
See application file for complete search history.

(56) References Cited

U.S. PATENT DOCUMENTS

| | | | |
|---|---|---|---|
| 6,289,074 B1 | 9/2001 | Arai et al. | |
| 8,031,828 B1 * | 10/2011 | DeMan | G06T 11/005 378/15 |
| 8,111,893 B2 * | 2/2012 | Chen | G06T 11/006 324/307 |

(Continued)

FOREIGN PATENT DOCUMENTS

EP  2022402 A1  2/2009

OTHER PUBLICATIONS

Meyer, E. et al., "Normalized Metal Artifact Reduction (NMAR) in Computed Tomography", Nuclear Science Symposium Conference Record (NSS/MIC), 2009 IEEE, Issue Date: Oct. 24 2009-Nov. 1 2009, on pp. 3251-3255, ISSN : 1082-3654, E-ISBN : 978-1-4244-3962-1, Print ISBN: 978-1-4244-3961-4, References Cited: 13.

*Primary Examiner* — Phillip A Johnston
*Assistant Examiner* — Hsien Tsai
(74) *Attorney, Agent, or Firm* — GE Global Patent Operation; Marc A. Vivenzio (57) ABSTRACT

Systems, methods and non-transitory computer readable media for imaging. The system includes one or more radiation sources and detectors configured to transmit x-ray radiation towards a subject for imaging a dynamic process in a ROI of the subject and to acquire projection data corresponding to the ROI, respectively. The system also includes a computing device operatively coupled to one or more of the radiation sources and the detectors. The computing device is configured to provide control signals for performing one or more reference scans for acquiring reference data from a plurality of angular positions around the subject and for performing one or more tomosynthesis scans using one or more tomosynthesis trajectories for acquiring tomosynthesis data following the onset of the dynamic process. Additionally, the computing device is configured to reconstruct one or more images representative of the dynamic process using the reference data and/or the tomosynthesis data.

20 Claims, 5 Drawing Sheets

(56) References Cited

U.S. PATENT DOCUMENTS

| | | | |
|---|---|---|---|
| 2005/0220265 A1* | 10/2005 | Besson | A61B 6/508 378/16 |
| 2005/0251010 A1 | 11/2005 | Mistretta et al. | |
| 2006/0067464 A1* | 3/2006 | Clinthorne | A61B 6/14 378/38 |
| 2007/0268994 A1 | 11/2007 | Chen | |
| 2009/0171244 A1 | 7/2009 | Ning et al. | |
| 2010/0202583 A1* | 8/2010 | Wang | A61B 6/032 378/9 |
| 2011/0013817 A1 | 1/2011 | Medow | |
| 2011/0026667 A1 | 2/2011 | Poorter | |
| 2011/0075794 A1 | 3/2011 | Boese et al. | |
| 2011/0280458 A1 | 11/2011 | Flohr et al. | |

* cited by examiner

SYSTEMS AND METHODS FOR IMAGING DYNAMIC PROCESSES

BACKGROUND

Interventional techniques are widely used for managing a plurality of potentially life-threatening medical conditions. Generally, interventional techniques may be employed in various fields of medicine such as neurology, general radiology, cardiology and electrophysiology. Specifically, interventional imaging systems may be used to visualize structural information, for example, anatomical details as well as injected contrast, catheters and other devices during an intervention that may be difficult to visualize using other imaging techniques.

Certain medical procedures, however, may also benefit from functional information in addition to structural information for facilitating the interventional procedure. Knowledge of functional information such as tissue perfusion parameters including regional blood volume, regional mean transit time, regional blood flow etc. are very useful in various medical scenarios. A surgeon may rely on these functional parameters for pre-procedure planning of endovascular treatments, for example, concerning cerebral vascular accidents such as a stroke, angioplasties of the carotid and placement of carotidian and intracranial stents. The surgeon may also use the functional parameters during the interventional procedure for evaluating the efficacy of the therapeutic procedure in real-time, and further for determining whether to stop or continue the procedure based on the evaluated effect.

Generally, an interventional procedure may be preceded by an initial patient exam using a magnetic resonance (MR) system or a computed tomography (CT) system for obtaining both structural and functional information for diagnosis and/or treatment. Subsequently, the patient may undergo therapy via an interventional procedure in a vascular operating theater. During the operation, an interventional device such as a catheter may be inserted into a vascular structure, allowing access to a region of interest (ROI), such as vessels of the brain for performing the interventional procedure. The insertion as well as the navigation of the catheter within the different branches of the vascular system, however, is a challenging procedure. Furthermore, use of separate or combined CT/MR systems for structural and functional imaging may involve frequent switching between the different imaging modalities, corresponding movement of patient and change in patient positions, catheter guidance, and/or therapeutic modes. Use of such systems, thus, may lead to complicated workflows and may not be suitable in all imaging scenarios due to size, cost and imaging time constraints.

These limitations are addressed in certain conventional interventional imaging approaches that employ C-arm systems for providing structural and functional information. These C-arm systems may include a source and a detector mounted on a movable arm configured to rotate relative to the center of an imaged volume. Particularly, the C-arm may be configured to move in a desired path so as to orient the source and detector at different positions and angles around a patient disposed on a table for acquiring corresponding projection data, while also allowing a physician to access the patient. In one conventional implementation, for example, the C-arm may be configured to acquire a spin dataset, that is, to rotate axially by about 180 degrees plus the fan angle around the long axis of the patient.

Further, the C-arm system may reconstruct the acquired projection data into two-dimensional (2D) and/or three-dimensional (3D) images using, for example, a filtered back-projection (FBP) or an algebraic reconstruction (ART) technique. The FBP approach, although fast, may introduce streaking artifacts that negatively impact image quality, and in turn, affect medical diagnosis and decision-making. In contrast, iterative methods based on ART may reduce image artifacts by using image priors but may suffer from longer computation times.

The scanning time for a conventional "spin" acquisition that rotates the C-arm around the patient is typically five or more seconds for acquiring sufficient projection data for reconstructing 2D and/or 3D images of desired image quality. Such a slow rotation rate, however, may result in image artifacts due to voluntary motion, such as due to patient repositioning, and involuntary motion such as peristalsis or heart motion within the patient. Additionally, the slow rotation rate may restrict usefulness of a C-arm system for imaging transient phenomena such as perfusion events and/ or device motion and guidance. For example, the slow rotation rate of the C-arm system may prove insufficient for imaging dynamic processes that require a faster temporal sampling than, for example, the 5 seconds afforded by a sequence of repeated spin acquisitions.

Moreover, a conventional spin geometry of the C-arm system may further complicate the scanning process as the conventional geometrical configuration entails scanning more than half way around the patient in one or more axial scans. Particularly, in the conventional spin configuration, a radiation source may rotate to positions above the patient table, which may significantly increase a chance of a collision of the C-arm with the table, the patient, other equipment and/or medical devices in the vicinity. Additionally, when positioned above the patient table, the radiation source may cause greater scatter, which in turn, may significantly increase the radiation exposure to the patient and/or a physician. The long scanning time, significant radiation exposure and the complicated workflow, thus, may render use of the conventional C-arm geometry unfeasible for real-time (or near real-time) interventional 3D imaging of dynamic processes.

BRIEF DESCRIPTION

In accordance with aspects of the present disclosure, systems, methods and non-transitory computer readable media for imaging are disclosed. Particularly, the imaging system includes one or more radiation sources configured to transmit x-ray radiation towards a subject for imaging a dynamic process in a ROI of the subject and one or more detectors configured to acquire projection data corresponding to the ROI. In an embodiment, the system also includes a computing device operatively coupled to one or more of the radiation sources and to the detectors. Further, in an embodiment, the computing device is configured to provide control signals for performing one or more reference scans for acquiring reference data from a plurality of angular positions around the subject. The computing device is further configured to provide control signals for performing one or more tomosynthesis scans using one or more tomosynthesis trajectories for acquiring tomosynthesis data following the onset of the dynamic process. Additionally, the computing device is also configured to reconstruct one or more images representative of the dynamic process using the reference data and/or the tomosynthesis data.

According to an embodiment of the present invention, there is provided an imaging method. The method comprises performing one or more reference scans for acquiring reference data from a plurality of angular positions around a subject; allowing for onset of a dynamic process in a region of interest of the subject; performing one or more tomosynthesis scans using one or more tomosynthesis trajectories for acquiring tomosynthesis data; and reconstructing one or more images representative of the dynamic process using the reference data, the tomosynthesis data, or a combination thereof.

According to an embodiment of the present invention, there is provided a non-transitory computer readable medium that stores instructions executable by one or more processors to perform a method for imaging, comprising: performing one or more reference scans for acquiring reference data from a plurality of angular positions around a subject; allowing for onset of a dynamic process in a region of interest of the subject; performing one or more tomosynthesis scans using one or more tomosynthesis trajectories for acquiring tomosynthesis data; and reconstructing one or more images representative of the dynamic process using the reference data, the tomosynthesis data, or a combination thereof.

BRIEF DESCRIPTION OF THE DRAWINGS

These and other features and aspects of embodiments of the present technique will become better understood when the following detailed description is read with reference to the accompanying drawings in which like characters represent like parts throughout the drawings, wherein.

DETAILED DESCRIPTION

The following description presents embodiments of systems and methods for imaging dynamic processes in real-time during interventional and/or surgical procedures. Particularly, certain embodiments describe systems and methods employing unconventional combinations of acquisition trajectories for imaging dynamic processes for use during minimally-invasive interventional procedures. The interventional procedures, for example, may include angioplasty, stent placement, removal of blood clots, localized thrombolytic drug administration, perfusion studies, balloon septostomy, Transcatheter Aortic-Valve Implantation (TAVI), tumor embolization and/or an electrophysiology study.

It may be noted that in the present description, the terms "dynamic process(s)" and "transient phenomena" have been used interchangeably to refer to processes and events where at least a portion of the subject to be imaged exhibits motion or other dynamic processes over time, such as, take-up and wash-out of a contrast medium. By way of example, the dynamic processes may include fluid flow through a passage, device vibrations, movement of an interventional device through a vascular structure, cardiac motion, respiratory motion, peristalsis, and/or change in tissue perfusion parameters including regional blood volume, regional mean transit time and/or regional blood flow.

Additionally, the following description presents embodiments of imaging systems and methods that minimize contrast agent dosage, x-ray radiation exposure and scan durations. Certain embodiments of the present systems and methods may also be used for reconstructing high-quality 3D cross-sectional images in addition to the 2D projection images for allowing diagnosis, therapy delivery, and/or efficacy assessment. Particularly, embodiments of the systems and methods may employ the unconventional yet efficient acquisition trajectories for faster and significantly less intrusive imaging of dynamic processes.

For discussion purposes, embodiments of the present systems are described with reference to use of a C-arm system employing unconventional acquisition trajectories for imaging a target region of the subject. In certain embodiments, the present systems and methods may be used during interventional or surgical procedures. Additionally, embodiments of the present systems and methods may also be implemented for imaging various transient phenomena in non-medical imaging contexts, such as security screening and/or industrial nondestructive evaluation of manufactured parts. An exemplary system that is suitable for practicing various implementations of the present technique is described in the following section with reference to FIG. 1.

Figure 1:
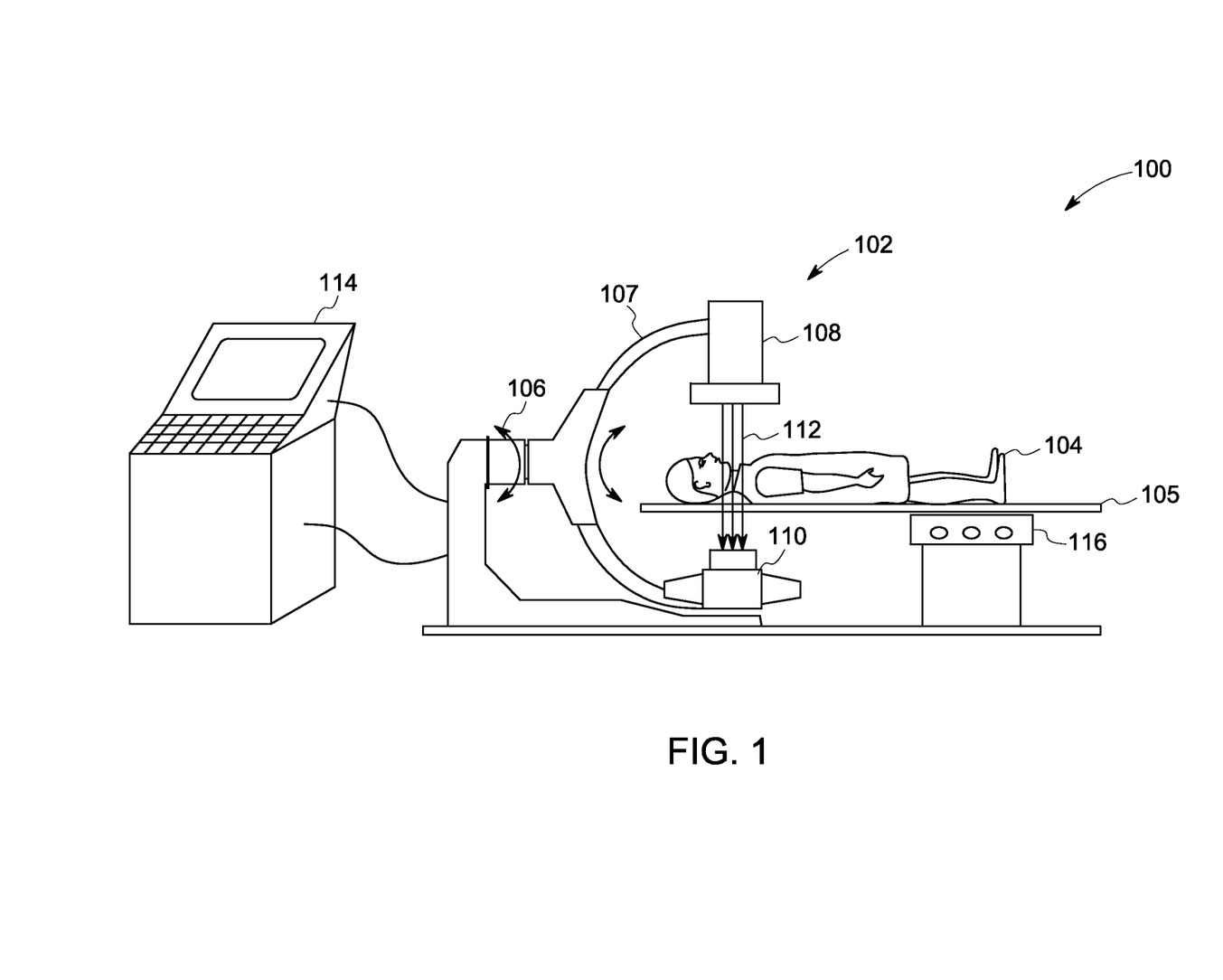
FIG. 1 is a schematic representation of an exemplary imaging system, in accordance with certain aspects of the present disclosure.

FIG. 1 illustrates an exemplary imaging system 100, for example, for use in interventional medical procedures. In one embodiment, the system 100 may include a C-arm system 102 configured to acquire projection data from one or more view angles around a subject, such as a patient 104 positioned on an examination table 105 for further analysis and/or display. To that end, the C-arm system 102 may include a gantry 106 having a mobile support such as a movable C-arm 107 including at least one radiation source 108 such as an x-ray tube and a detector 110 positioned at opposite ends of the C-arm 107.

In certain embodiments, the radiation source 108 may include multiple emission devices, such as one or more independently addressable solid-state emitters arranged in one or multi-dimensional field emitter arrays, configured to emit the x-ray beams 112 towards the detector 110. Further, the detector 110 may include a plurality of detector elements that may be similar or different in size and/or energy sensitivity for imaging a region of interest (ROI) of the patient 104 at a desired resolution.

In certain embodiments, the C-arm 107 may be configured to move along a desired scanning path for orienting the x-ray source 108 and the detector 110 at different positions and angles around the patient 104 for acquiring information for 3D imaging of dynamic processes. Accordingly, in one embodiment, the C-arm 107 may be configured to rotate about a first axis of rotation. The angular range of the C-arm 107 about the first axis, for example, may approximately be about plus or minus 120 degrees relative to a reference position. Additionally, the C-arm 107 may also be configured to rotate about a second axis in an angular movement with a range of about plus or minus 60 degrees relative to the reference position. In certain embodiments, the C-arm 107 may also be configured to move forwards and/or backwards along the first axis and/or the second axis.

Accordingly, in one embodiment, the C-arm system 102 may include control circuitry 114 configured to control the movement of the C-arm 107 along the different axes based on user inputs and/or protocol-based instructions. To that end, in certain embodiments, the C-arm system 102 may include circuitry such as tableside controls 116 that may be configured to provide signals to the control circuitry 114 for adaptive and/or interactive control of imaging and/or processing parameters using various input mechanisms. The imaging and/or processing parameters, for example, may include display characteristics, x-ray technique and frame rate, scanning trajectory, table motion and/or position, and gantry motion and/or position.

In certain embodiments, the control circuitry 114 may be configured to use user-specified and/or protocol-based imaging and/or processing parameters to move the C-arm 107 in certain unconventional acquisition trajectories, thus allowing greater flexibility in data acquisition. Use of the unconventional acquisition trajectories may allow for faster data acquisition, and in turn, faster sampling or refresh rates during imaging to allow the physician to monitor various dynamic processes in real-time. For example, the acquisition trajectories may be used to generate image sequences that aid in real-time monitoring of movement of an interventional device through the vasculature and/or a detailed evaluation of the change in perfusion parameters, for example, owing to contrast agent administration, medication, ablation and/or the interventional procedure. Certain exemplary configurations of an imaging system that allow for real-time imaging of dynamic processes using unconventional acquisition trajectories will be described in greater detail with reference to FIG. 2.

Figure 2:
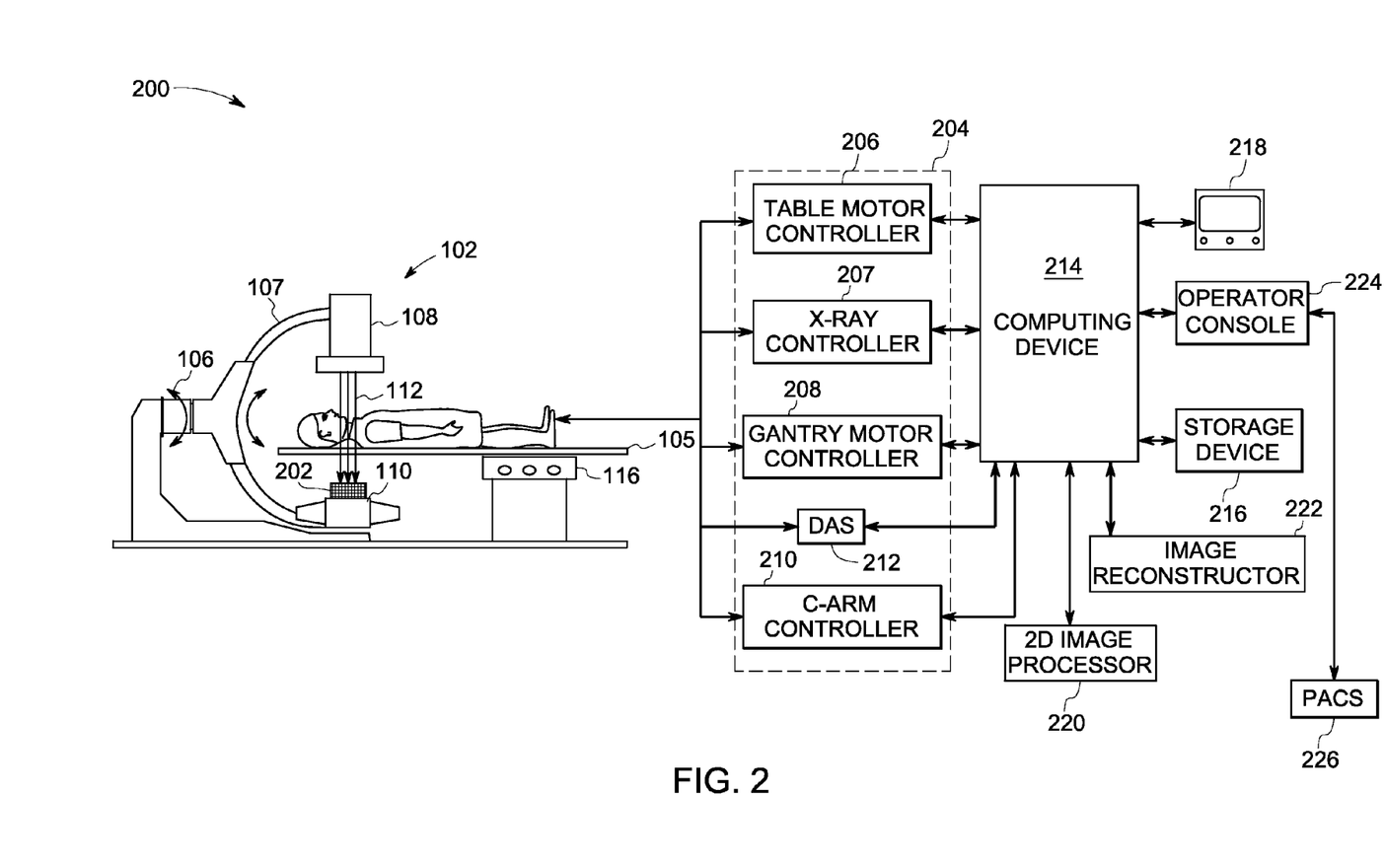
FIG. 2 is a schematic representation of another exemplary embodiment of an imaging system, in accordance with certain aspects of the present disclosure.

FIG. 2 is a diagrammatic illustration of exemplary components of an imaging system 200, similar to the system 100 of FIG. 1, for imaging dynamic processes. As previously noted, the dynamic processes may include object motion, physiological motion or other dynamic processes that evolve over time, such as, take-up and wash-out of a contrast medium. To that end, in one embodiment, the radiation source 108 projects, for example, fan-shaped or cone-shaped x-ray beams 112 for imaging a target ROI of the patient 104. Particularly, the system 200 configures one or more parameters of the radiation source 104 to direct the x-ray beams 112 on the target ROI based on a designated configuration of the detector 110 and/or a desired imaging protocol.

In certain embodiments, the detector 110 may include a plurality of detector elements 202, for example, arranged as a 2D detector array for sensing the projected x-ray beams 112 that pass through the patient 104. In one embodiment, the detector elements 206 produce an electrical signal representative of the intensity of the impinging x-ray beams 112, which in turn, can be used to estimate the attenuation of the x-ray beams 112 as they pass through the patient 104. In another embodiment, the detector elements 202 determine a count of incident photons in the x-ray beams 112 and/or determine corresponding energy.

In certain embodiments, the detector 110 corresponds to a hybrid detector that includes a combination of one or more energy integrating (EI) and/or energy discriminating (ED) detector elements 202 that provide energy absorption and distribution information, respectively, for use in characterizing tissue type, which in turn, may be useful for diagnosing a pathological condition of the patient 104. Additionally, the system 200 may selectively configure the detector elements 202, for example, by selectively operating smaller detector elements 202 for generating high-resolution 2D projection images and larger detector elements 202 for generating high-fidelity 3D volumetric images. Alternatively, the signals of smaller detector elements 202 may be combined to form larger detector elements 202 prior to signal digitization, thus resulting in a faster readout for 3D volumetric acquisitions.

Particularly, in one embodiment, the detector elements 206 may acquire electrical signals corresponding to the generated x-ray beams 112 at a variety of angular positions around the patient 104 for collecting a plurality of radiographic projection views for image construction. To that end, the system 200 may include a control mechanism 204 configured to control position, orientation and/or rotation of the table 105, the gantry 106, the C-arm 107 and/or the components mounted thereon in certain specific acquisition trajectories.

The control mechanism 204, for example, may include a table motor controller 206, which allows control of the position and/or orientation of the table 105 based on a protocol-based instruction and/or an input received from the physician, for example, via tableside controls, such as a joystick. During an intervention, for example, the physician may grossly position an interventional device in the patient 104 in the field of view of the system 102 by moving the table 105 using the table motor controller 206. Once the interventional device can be visualized, the physician may advance position of the interventional device within the vasculature and performs a diagnostic procedure or a therapeutic procedure. The table motor controller 206, thus, may be configured to allow for a greater range of patient positions for facilitating the intervention at a target ROI even in larger patients.

In certain embodiments, the x-ray source 108 and the detector 110 for interventional imaging may be controlled using an x-ray controller 207 in the control mechanism 204, where the x-ray controller 207 is configured to provide power and timing signals to the radiation source 108 for controlling x-ray exposure during imaging. Further, the control mechanism 204 may also include a gantry motor controller 208 that may be configured to control the rotational speed, tilt, view angle, and/or position of the gantry 106. In one embodiment, the gantry motor controller 208 may provide control signals for moving the gantry 106 forward and backward to position the system 102 with respect to the patient 104 on the table 105 via rails or other mechanical mechanisms. Further, gantry view angle and tilt may be used to specify the view angle of projection images, thus providing the physician with the desired projection of the target ROI.

In certain embodiments, the control mechanism 204 also includes a C-arm controller 210, which in concert with the gantry motor controller 208, may be configured to move the C-arm 107 in certain unconventional combination of acquisition trajectories for real-time imaging of dynamic processes occurring in a target ROI. In certain other embodiments, imaging systems having one or more sources and detectors capable of moving independently of each other may be used for implementing the imaging geometries associated with the unconventional combination of acquisition trajectories. In certain further embodiments, system configurations where source and detector are not directly connected via a C-arm, and where they can be positioned independently, may be used. Alternatively, the system 200 may use one or more stationary and/or moveable arrays of sources, for example, including individually addressable source points with a single detector, a large-area detector or multiple detectors to minimize moving parts and/or the range of the required motion trajectory, thus further enhancing non-intrusiveness during an imaging scan.

In certain embodiments, the control mechanism 204 may configure the gantry 106 to perform a limited angle tomosynthesis scan for facilitating faster data acquisition through use of a smaller scanning range. In certain other embodiments, the control mechanism 204 may configure the gantry 106 to perform the tomosynthesis scan using, for example, one or more closed or open acquisition trajectories, which minimize scanning time and allow acquisition of sufficient projection data for use in imaging dynamic processes in real-time.

In one embodiment, the closed acquisition trajectories may include cyclical trajectories that may be bound by (or within) a circle of a particular or determined radius x. A geometrical characteristic such as a radius of the acquisition trajectories may be selected based on a time constant of a dynamic process being observed and/or imaged. Particularly, in certain embodiments, the tomosynthesis trajectories may be chosen such that the trajectories are bound within a circle of a determined radius, where the determined radius depends upon the time constant of the dynamic process and/or where the circle radius is also a function of maximum gantry speed and acceleration (due to safety and gantry capability considerations). Typically, for dynamic processes requiring a faster update rate, the trajectories may be bounded by a smaller circle, while for processes with a slower update rate, the trajectories may be bounded by a larger circle.

Further, the open acquisition trajectories may include, for example, linear, multi-line, helical, and/or spiral trajectories, trajectories that run in opposite directions and/or trajectories that include partial traversal of a closed acquisition trajectory. Certain exemplary embodiments of closed and open trajectories will be discussed in detail with reference to FIGS. 3-7.

Figure 3:
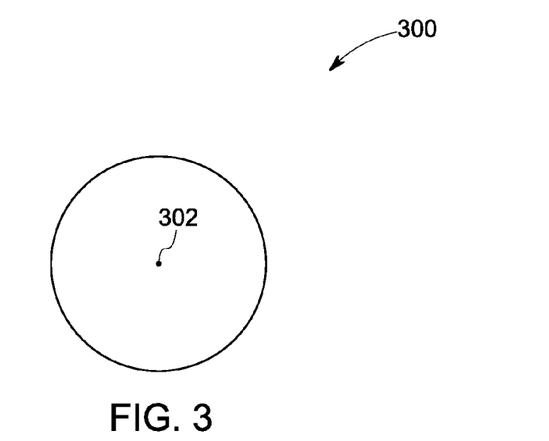
FIGS. 3, 4, and 5 are schematic representations of exemplary embodiments of closed acquisition trajectories used by the imaging system, in accordance with certain aspects of the present disclosure.
Figure 4:
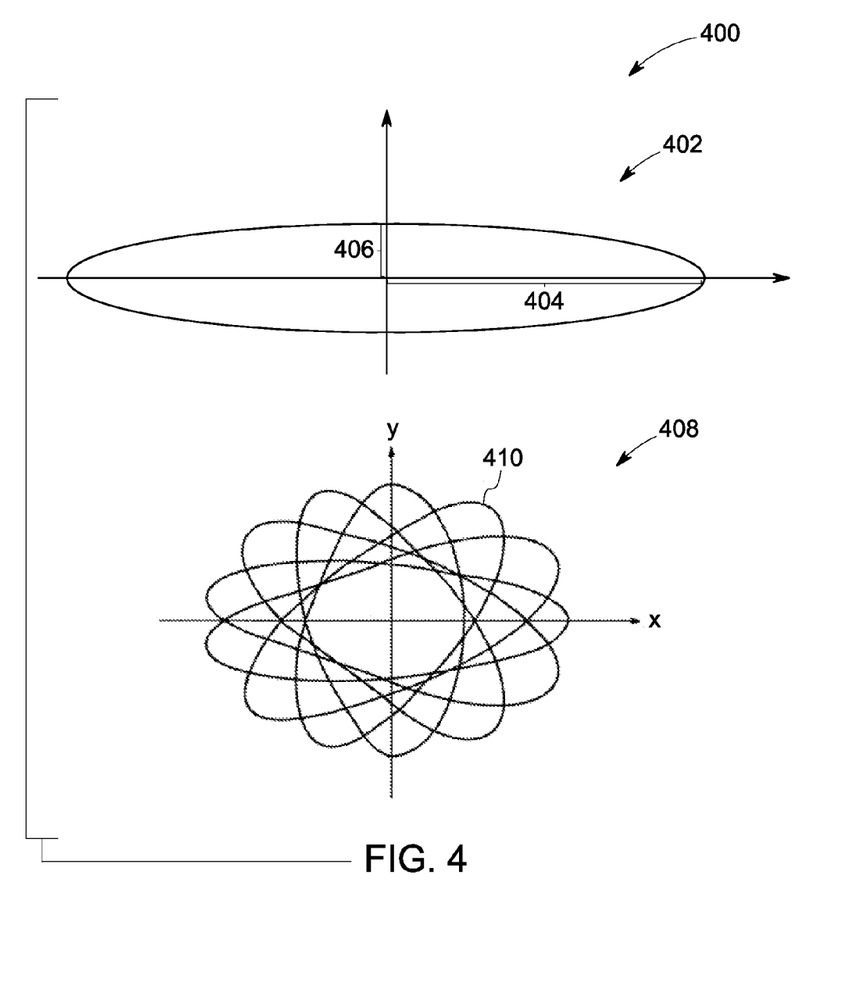
Figure 5:
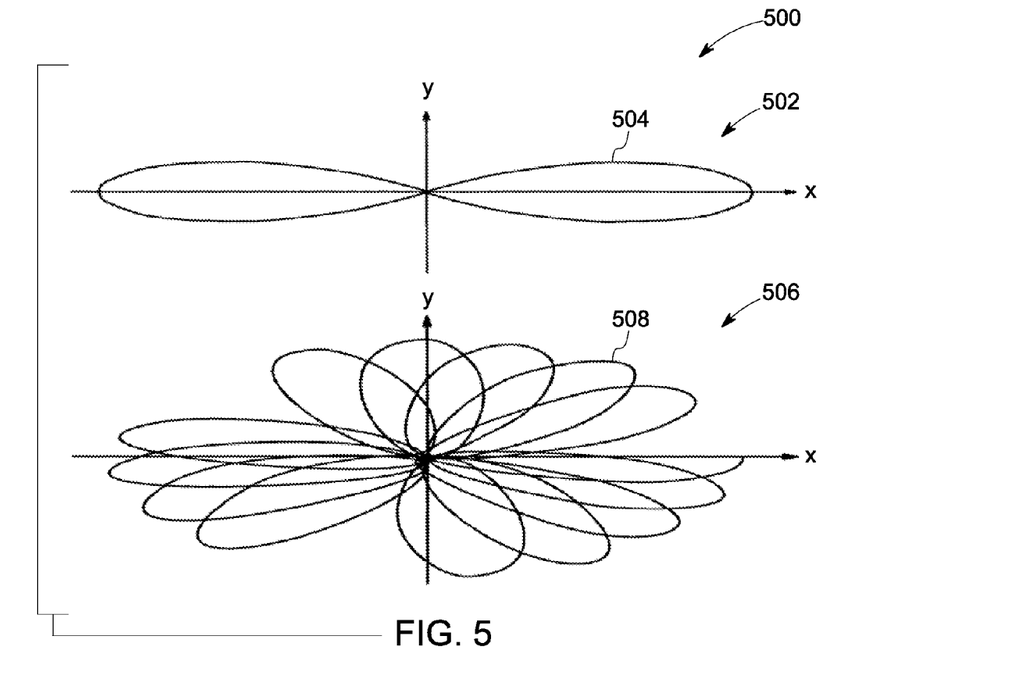

Generally, the closed acquisition trajectories may include cyclical trajectories including, for example, circles, ellipses, helixes, spirographs (hypotrochoids and/or hypocycloids), figure-8 shaped trajectories, or combinations thereof. FIGS. 3-5 illustrate examples of some of the closed acquisition trajectories for use in the limited-angle tomosynthesis scan. Particularly, FIG. 3 illustrates a schematic representation 300 of a circular trajectory 302, for example, with the radiation source 108 confined to a plane parallel to, or an angle to a patient table plane. The circular trajectory 302 may be supplemented with a point at the center of the circle, multiple concentric circles and/or spiral trajectories. In certain embodiments, the circular trajectory 302 may allow for continuous data acquisition through actual and/or mimicked movement, for example, of the radiation source 108 and/or the detector 110 in the same or different directions.

FIG. 4 illustrates a schematic representation 400 of certain other embodiments of a closed scanning trajectory. Particularly, FIG. 4 illustrates an exemplary elliptical scanning trajectory 402 having a major axis 404 and a minor axis 406. Alternatively, an elliptical scan 408 with a curve 410 may be achieved with additional cyclical rotation of the major axis.

Further, FIG. 5 illustrates a schematic representation 500 of a closed trajectory forming a figure-8 shape or a looped scan 502, in which a loop 504 is traversed as the tomosynthesis scanning path. Although FIG. 5 illustrates a looped scan 502 with only two loops 504, in certain embodiments, the loop-shaped scan may include a greater number of loops being traversed in one or more angular orientations. For example, element 506 illustrates an interlaced spirograh or a flower-shaped trajectory 508 implemented by rotating the loop-axis.

Figure 6:
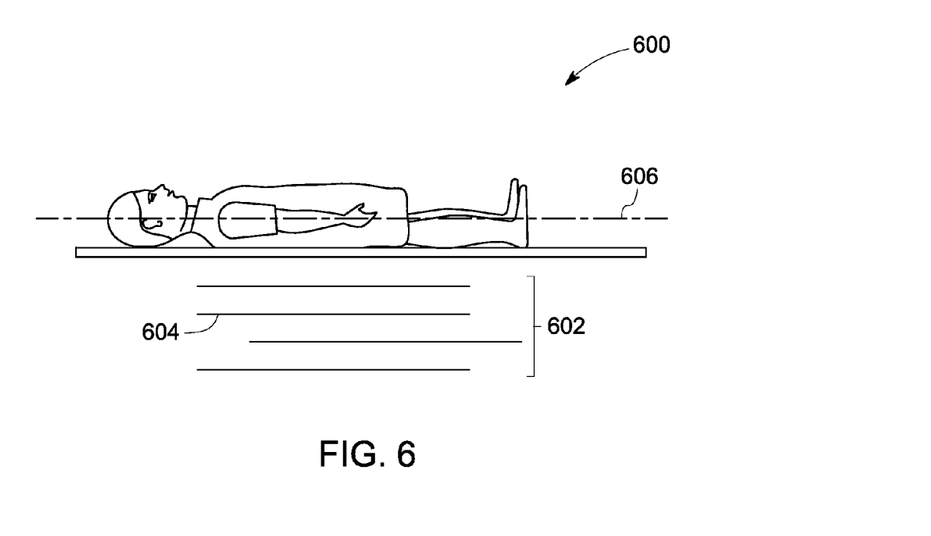
FIGS. 6-7 are schematic representations of exemplary embodiments of open acquisition trajectories used by the imaging system, in accordance with certain other aspects of the present disclosure.
Figure 7:
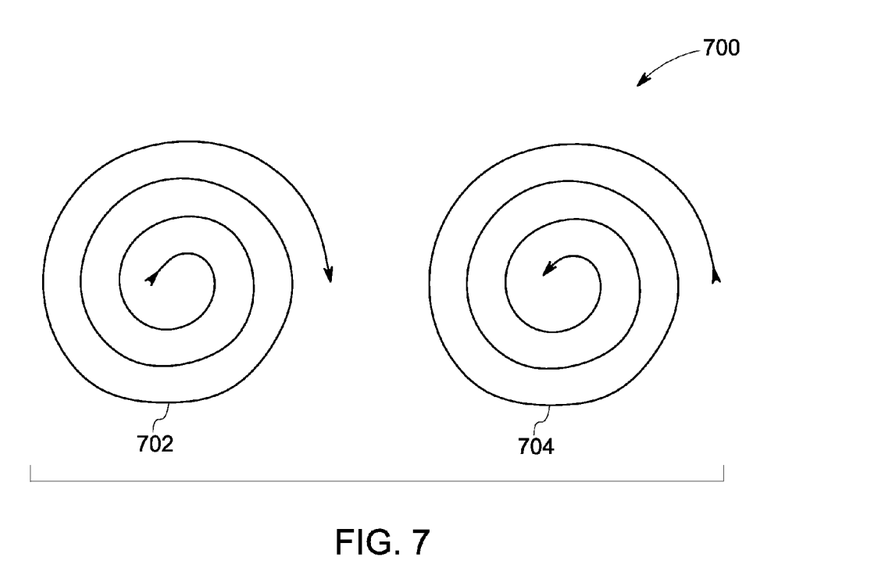

FIGS. 6-7 illustrate examples of open acquisition trajectories for use during the tomosynthesis scan. Specifically, FIG. 6 illustrates a schematic representation 600 of a multi-line scanning trajectory 602 with a focus moving back and forth over multiple lines 604 below a patient table plane 606. The lines 604 may be in any orientation and/or location below the patient table plane 606 such that the x-ray beam 112 (see FIG. 1) passes through the patient 104. Further, FIG. 7 illustrates a schematic representation 700 of an embodiment of another open acquisition trajectory 702 having a spiral construction. In one embodiment, the spiral trajectory 702 may allow reversal of the scanning direction (as shown in element 704), for example, on completion of the spiral.

As previously noted, the various trajectories illustrated in FIGS. 3-7 may be implemented using one or more sources and detectors capable of moving independently of each other. Alternatively, the tomosynthesis trajectories may be implemented using a multi-spot radiation source, a large-area detector and/or multiple detectors having individually addressable source and detector elements configurable to mimic desired motion of the radiation source 108 and/or the detector 110. Additionally, in certain embodiments, one or more additional source and detector points may be employed to supplement defined trajectories for enhancing the quality of the acquired projection data and providing for better interventional imaging.

With returning reference to FIG. 2, the system 200 may use the projection data acquired using the closed and/or open acquisition trajectories, such as illustrated in FIGS. 3-7, for image reconstruction. Particularly, in one embodiment, the system 200 may perform a reference scan with a spin trajectory of about 180 degrees plus fan angle or a large-angle tomosynthesis scan prior to administering the contrast agent and performing the tomosynthesis scan as discussed herein above. In certain embodiments, the reference scan, for example, may include a single-orbit nominal tomosynthesis trajectory augmented by additional views, such as, by a denser sampling along the trajectory, by a scanning trajectory with a larger tomographic angle, or a spin, etc. The acquired projection data may be used to reconstruct one or more reference images using, for example, an FBP or an iterative image reconstruction technique.

In one embodiment, the control mechanism 204 may include a data acquisition system (DAS) 212 for sampling the projection data from the detector elements 206 and converting the analog data to digital signals for image reconstruction. Moreover, in certain embodiments, the data sampled and digitized by the DAS 212 may be input to a computing device 214. Alternatively, in certain embodiments, the computing device 214 may store the projection data in a storage device 216, such as a hard disk drive, a floppy disk drive, a compact disk-read/write (CD-R/W) drive, a Digital Versatile Disc (DVD) drive, a flash drive, or a solid-state storage device for further evaluation.

In certain embodiments, the computing device 214 may include modules and/or applications that allow for automated analysis of the acquired projection data, for example, for estimating the location of a target ROI for further evaluation and/or extraction of anatomical and/or functional information associated with the target ROI. In one embodiment, the target ROI may correspond to at least a portion of a desired area of interest of the patient 104 that was imaged during the reference scan. The computing device 214 may use the preliminary scan data and/or images, for example, using automated analysis tools to supplement the projection data acquired using the tomosynthesis scan with additional information for allowing for reconstruction of improved images that characterize functional and structural information of the target ROI with greater accuracy.

Particularly, embodiments of the system 200 may employ the C-arm system 102 for providing projection (2D) or volumetric (3D) images of dynamic processes evolving at the target ROI. To that end, in one example, a contrast agent, for example including an x-ray opaque iodine-based colorless "dye," is injected into the vasculature using a catheter to accentuate the absorption of x-rays, thus improving visualization of blood vessels in the vicinity of the catheter tip. Further, the C-arm system 102 may be configured to continually measure 2D projection data and present one or more contrast-enhanced images of the patient 104 on a display 218 in real-time, and/or to evaluate 2D/3D information for presentation on the display 218 based on clinical requirements.

To that end, in one embodiment, C-arm system 102 includes a 2D image processor 220 for reconstructing high-fidelity 2D images in real-time for use during the interventional procedure. By way of example, the 2D image processor 220 may process the projection data to analyze the 2D images for tracking movement of the interventional device within the patient's body in real-time. Generally, for real-time hand-eye coordination, it is desirable that the time starting from the instant at which the interventional device is moved, the detector 110 is read out, the acquired data is processed and subsequently loaded onto the display 218 for display in real-time to be less than 150 milliseconds.

Use of the dedicated 2D image processor 220 allows for a separate 2D image processing chain that aids in generating low-latency 2D images and corresponding diagnostic information. The low-latency 2D images and/or information, in turn, may be advantageously used for illustrating changes in perfusion parameters, enabling eye-hand coordination for interventional device guidance and/or depicting efficacy of the interventional procedure in real-time. In certain embodiments, the 2D image processor 220 may also use the projection data for reconstructing 3D volumetric images of smaller target regions centered around the catheter tip or small angular ranges (for example, less than 180 degrees) in real-time, or near real-time to the user, thus providing functionality typically not available with conventional imaging systems.

Further, in one embodiment, the 3D cross-sectional images (or 3D volumes) may be generated as per an imaging requirement by an image reconstructor 222 operatively coupled to the computing device 214. Particularly, in certain embodiments, the 3D images may be representative of the dynamic process evolving in the target ROI. Accordingly, the 3D images may include two or more 3D volumes, with each 3D volume being representative of the state of the imaged object, for example, representative of contrast/iodine concentration at a sample in time. In certain other embodiments, each (of one or more) reconstructed 3D volume may correspond to a parameter indicative of at least one local characteristic the dynamic process, such as a rate of contrast uptake, a rate contrast washout and/or cerebral blood volume. And in some embodiments, each of the two or more 3D volumes comprises a sample in time.

By way of example, during a perfusion study following a stroke, the image reconstructor 222 may be configured to generate one or more 3D images of the brain for display on the display device 218 for evaluation and/or intervention. In this embodiment, the generated 3D volumetric images may represent (or characterize) the uptake and washout of contrast. Particularly, in one embodiment, the generated images may be used for assessing whether blood flow has been sufficiently restored by the intervention, or whether further treatment (for example, intra-arterial injection of thrombolytic drugs) is necessary. In another embodiment, during a cardiac evaluation, the method may be used to assess whether functional ischemia is associated with a cardiac stenosis by estimating heart wall motion and/or tissue perfusion parameters and/or to assess if revascularization may provide clinical benefit.

Typically, non-invasive imaging for functional assessment aims to identify the patients that will benefit from the percutaneous intervention in a catheterization laboratory. To that end, in one embodiment, the C-arm system 102 may be configured to acquire projection data at the determined time points and angular positions in real-time during interventional imaging for generating contrast enhanced images for estimating, for example, cerebral perfusion parameters such as cerebral blood flow, cerebral blood volume and/or flow of contrast into the two cerebral hemispheres. The estimated cerebral perfusion parameters, in turn, may be used by the C-arm system 102 to assess the brain perfusion prior to, during and after the intervention. In certain embodiments, the 3D images may also be used for providing catheter guidance during the interventional procedure.

In certain scenarios, using only the limited angle tomosynthesis datasets may not be sufficient for reconstructing a high-quality volumetric image of the target ROI. Furthermore, use of conventional reconstruction techniques, such as FBP, for reconstruction images using incomplete tomosynthesis datasets may result in images with streaking artifacts. Such streaking artifacts may negatively affect image quality and limit the use of images in any related decision-making processes. Accordingly, in certain embodiments, the image reconstructor 222 use the reference scan images and/or information derived therefrom to supplement the tomosynthesis scan data during image-reconstruction.

Additionally, in certain further embodiments, the image reconstructor 222 may use compressed-sensing or sparsity-constrained solutions for generating high-quality images of the target ROI even with the incomplete tomosynthesis datasets. Particularly, in one embodiment, the image reconstructor 222 may apply data differencing to reference scan and tomosynthesis scan data and/or images followed by sparsity-constrained image reconstruction. In one embodiment, data is differenced/subtracted in the projection domain. In another embodiment, the projection data to be used in the subtraction (and corresponding to the reference scan) is computed using a re-projection of a previously computed 3D volume corresponding to the patient anatomy without injected contrast. In a further embodiment, both reference data and tomosynthesis data may be used in a joint reconstruction process.

Specifically, the image reconstructor 222 may employ an iterative approach to image reconstruction, where sparsification may be applied, for example, in both data and image domains. Iterations may be configured such that high intensity objects are reconstructed first and low intensity objects are gradually added by varying the degree of sparsification in image and/or data domains. In one embodiment, varying the degree of sparsification may be achieved in a computationally efficient way by approximately adjusting threshold levels Sparsity-constrained reconstruction, thus, may allow for reconstruction of high-quality images from relatively few (100, 10 or less) input projections, for example, during interventions for real-time catheter guidance and/or functional and structural assessment.

In certain embodiments, the display device 218 may be configured to output the reconstructed images in real-time, periodically and/or based on user input. To that end, the display device 218, for example, may include one or more monitors, printers or display means integrated into wearable eyeglasses. Further, the display device 218 may be table-mounted, ceiling-mounted or cart-mounted to allow an operator to observe real-time 2D projection images, reconstructed 3D images, or a combination of 2D and 3D images, as well as data derived therefrom, and other relevant information such as exposure time and/or contrast dose used at different points of time during the procedure based on protocol-based and/or user input. In an embodiment, the display device 218 is operatively coupled to the computing device 214 and configured to display the one or more images representative of the dynamic process based on one or more imaging specifications, user input, or a combination thereof.

In one embodiment, the system 200 may include an operator console 224 that may be configured to allow selection and display of scanning modes, FOV, prior exam data, and/or intervention path. The operator console 224 may also allow on-the-fly access to 2D and 3D scan parameters and selection of an ROI for subsequent imaging, for example, based on operator and/or system commands. In one example, the operator console 224 may be used to control display of post-processed reconstructed images to focus on specific regions for assessing a nature and extent of disease in the patient 104. In another example, the operator console 224 may allow fetching and display of patient data from associated sensors such as an ECG monitor, an MR system, an ultrasound system, an optical imaging system or prior examination sequences stored in the storage device 216.

Accordingly, in one embodiment, the operator console 224 may include devices such as an interactive graphical user interface, a touch screen, a joystick and/or a tableside mouse. The interactive user interface may include menu and control options to allow the physician, for example, to select and configure the x-ray imaging protocol, select an acquisition trajectory, manage radiation dose in real-time, control gantry angular orientation, gantry tilt, gantry position, table motion and/or orientation and other parameters for imaging during reference and/or tomosynthesis scans. Moreover, the interactive user interface may also allow identification of a pathological ROI, display of the position of a catheter and/or surrounding tissues in relation to the ROI on the display 218, or navigation of the catheter past a tortuous section of vasculature in real-time.

Although FIG. 2 illustrates only one operator console 224, more than one operator interfaces may be coupled to the C-arm system 102, for example, for inputting or outputting system parameters, requesting examinations and/or viewing images. Further, in certain embodiments, the system 200 may be coupled to multiple displays, printers, workstations, a picture archiving and communications system (PACS) 226 and/or similar devices located either locally or remotely, for example, within an institution or hospital, or in an entirely different location via communication links in one or more configurable wired and/or wireless networks such as a hospital network and virtual private networks. In an exemplary implementation, the PACS 226 may be further coupled to a remote system such as a radiology department information system, hospital information system and/or to an internal or external network (not shown) to allow access to the image data.

Embodiments of the system 200, thus, allow for more efficient interventional imaging by using limited-angle tomosynthesis and sparsity-constrained image reconstruction for rapidly reconstructing artifact-free, quantitatively accurate images of the patient 104. Faster acquisition and rapid reconstruction, in turn, allows for motion characterization and perfusion studies, interventional imaging, device guidance, and/or other clinical applications to be performed in real-time using a single system, thus curtailing equipment and examination costs. Exemplary embodiments of a method for faster and more efficient diagnostic imaging using embodiments of the present system in accordance with certain aspects of the present disclosure will be described in greater detail with reference to FIG. 8.

Figure 8:
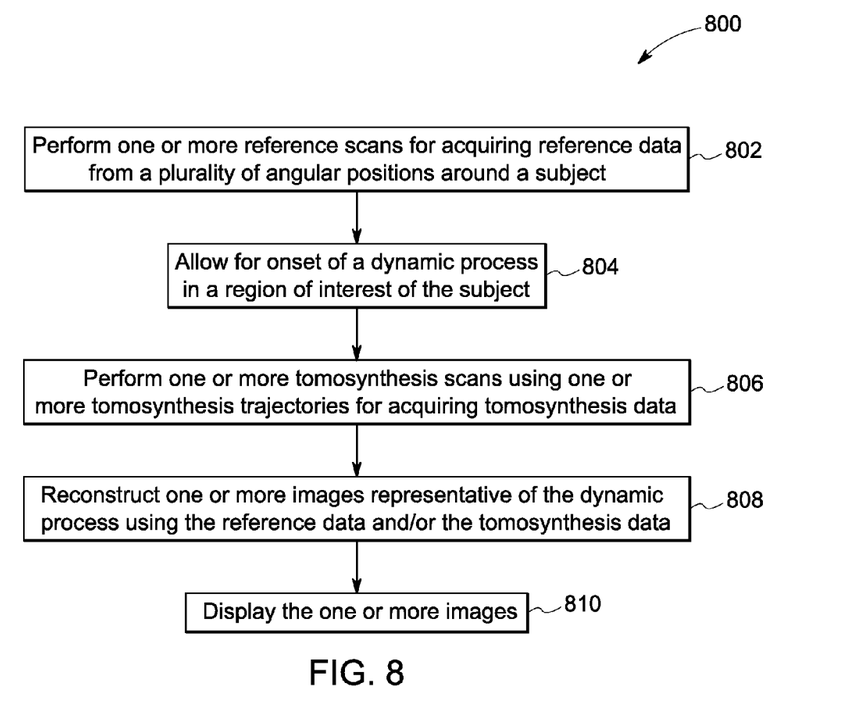
FIG. 8 is a flow diagram illustrating an exemplary method for imaging a subject, in accordance with certain aspects of the present disclosure.

FIG. 8 illustrates a flow chart 800 depicting an exemplary method for imaging dynamic processes in real-time using specific acquisition trajectories and/or reconstruction algorithms. Embodiments of the exemplary method may include computer executable instructions on a computing system or a processor. Generally, computer executable instructions may include routines, programs, objects, components, data structures, procedures, modules, functions, and the like that perform particular functions or implement particular abstract data types. Embodiments of the exemplary method including computer executable instructions may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 8, the exemplary method is illustrated as a collection of blocks in a logical flow chart, which include certain operations that may be implemented in hardware, software, or combinations thereof. The various operations are depicted in the blocks to illustrate the functions that are performed, for example, during the reference scan, tomosynthesis scan, and image reconstruction phases of the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIGS. 1-2.

Knowledge of functional information such as tissue perfusion parameters in addition to the structural characteristics is very useful for diagnosis and decision-making A surgeon may rely on the functional parameters, for example, for pre-procedure planning of an interventional procedure, evaluating efficacy of a therapeutic procedure in real-time, and further for determining whether to stop or continue the procedure based on the evaluated effect. Generally, interventional imaging may include an initial patient exam using a MR, CT or a C-arm system.

Embodiments of the present method describe techniques for enhanced imaging of high-quality 3D cross-sectional images using a C-arm system. To that end, at step 802, one or more reference scans may be performed for acquiring reference data from a plurality of angular positions around a subject, such as a patient. In one embodiment, at least one of the reference scans is performed using a full spin trajectory, for example, of about 180 degrees plus fan angle. In another embodiment, the reference scan may be performed using a large-angle tomosynthesis trajectory for acquiring reference data from a target ROI. In a further embodiment, a reference scan is acquired by using a nominal tomosynthesis trajectory. In yet another embodiment, the nominal tomosynthesis trajectory for acquisition of the reference scan data is augmented with additional views, or with additional trajectory segments. It may be noted that, in one embodiment, the reference scan may generally be acquired before the injection of contrast, or before the insertion of a catheter etc., that is, generally before the onset of the dynamically evolving process. In certain embodiments, the reference data may be used to reconstruct one or more reference images of the target ROI, for example, using an FBP or an iterative reconstruction technique.

Further, at step 804, an onset of the dynamic process may be allowed. To that end, a contrast agent may be administered to the patient for imaging the dynamic process. The contrast agent, for example, may include an iodine-based colorless "dye," for example, injected intra-arterially into the patient using an interventional device such as a catheter. Particularly, the contrast agent increases opacification of the blood proximal to an administration site, and thus, facilitates identification of the vasculature from nearby overlapping and confounding anatomical structures. Additionally, the contrast agent may be administered as an intravenous infusion, for example, for imaging of cerebral tissues. Alternatively, for certain applications, a bolus injection of the contrast agent may be administered, where a large quantity of the contrast agent is rapidly injected into the patient via an intravenous site. Administration of the contrast agent enhances visualizations, thus aiding in more accurate assessment of the dynamic process such as change in perfusion parameters and/or movement of the catheter through the vasculature.

Further, at step 806, one or more tomosynthesis scans are performed using one or more tomosynthesis trajectories for acquiring tomosynthesis data. The tomosynthesis scans may be limited angle scans performed using one or more specific tomosynthesis trajectories, such as discussed with reference to FIGS. 3-7. As previously noted, the tomosynthesis trajectories may include open and/or closed trajectories including, for example, circles, ellipses, loops, spirals, helixes, linear or multi-line trajectories, or combinations thereof. Generally, data acquisition using the tomosynthesis trajectory is performed continuously during the dynamic process, until some logical endpoint is reached. The logical endpoint, for example, may include an (expected) time when the contrast bolus has cleared the ROI (in the case of a perfusion study) and/or a time when correct placement of a device has been achieved.

In one embodiment, a continuous tomosynthesis scan may be initiated before the onset of the dynamic process, and the first set of acquired projection data serves as a reference scan. The dynamic process may then be initiated (for example, through injection of contrast, or insertion of a device) after a first part of the tomosynthesis scan has been completed. The scan completion, for example, may correspond to collection of sufficient data representing a reference scan. The data acquired using the tomosynthesis trajectories, in one embodiment, may be representative of contrast-enhanced intermediate projection data corresponding to the dynamic process in the target ROI.

In one embodiment, data differencing/image subtraction may be performed to determine a difference between the reference data and the intermediate data. As previously noted, the data may be differenced in the projection domain. Particularly, the tomosynthesis data may be subtracted from the reference data for cancelling the static structures, thus resulting in significantly sparser images. In the sparsified image, significantly fewer image pixels have significant image values.

Accordingly, at step 808, two or more images representative of the dynamic process may be reconstructed using the reference data and/or the tomosynthesis data. The images, for example, may be reconstructed using the determined difference between the reference data and the tomosynthesis data. Particularly, in one embodiment, a sparsity-constrained image reconstruction technique may be employed for reconstructing images, for example, representative of changes in contrast concentration, perfusion parameters and/or movement of the catheter in the vascular structure. Specifically a sparsified image having reduced streaking artifacts from the subtracted intermediate data set may be reconstructed. Subsequently, the sparsified image may be transformed into one or more images that represent the events corresponding to the dynamic process being imaged by solving a constrained minimization problem.

In certain embodiments, embodiments of the present disclosure allow continuous generation of a collection of 3D volumetric images that are representative of the dynamic state of an object. For real-time catheter navigation, certain embodiments of the present disclosure may operate in a 2D data acquisition mode to generate 2D projection images. The reconstructed images may then be displayed on a display, at step 810, for example, for further evaluation by the physician. In one embodiment, the physician may use the images for tracking the location of the interventional device through the vasculature, for example, based on the images rendered on the display, or by injection of a bolus of contrast agent to facilitate location of the catheter tip in the processed images. Alternatively, the computing device, such as the computing device 214 (see FIG. 2) may identify the interventional device location based on automated analysis of the reconstructed 3D images and/or the acquired projection data.

In certain embodiments, information derived from the reconstructed images may be displayed and used for exam prescription, planning and monitoring the interventional procedure. In one example, the reconstructed images may be used for determining functional parameters such as blood flow for ascertaining efficacy of the interventional procedure. In another example, the reconstructed images may also facilitate placement of a stent at a location of stenosis in a coronary vessel or carotid vessel, and/or placement of a clip in a location of an aneurysm, such as in the brain. The reconstructed images may further be used for local administration of thrombolytics to remove a clot such as in the brain, physical removal of a thrombosis at the site of occlusion and/or local administration of material to occlude vessels such as for tumor embolysis.

Similarly, the reconstructed cross-sectional images may also be displayed for use in functional assessment of the anatomy, as with neuro and cardiac CT perfusion. Additionally, the reconstructed images may be used to determine if the interventional procedure is complete. For example, one or more 3D images of the target ROI may be generated to assess a change in functional and/or structural characteristics, such as, improvement in the perfusion values of the target ROI after the intervention. It may be noted that the examples listed above for utilization of imaging data are not meant to be limiting, but are intended to only provide examples of the broad-based applicability of embodiments of the system 200 to different imaging scenarios.

Embodiments of the present systems and methods, thus, allow use of limited-angle tomosynthesis that employs less-intrusive scanning trajectories that provide good image quality, while reducing radiation scatter to the patient and/or the physician during the intervention. Particularly, the limited range tomosynthesis allows faster and less intrusive acquisition of data for 2D projection images and/or 3D volumetric images, which in turn enables characterization and evaluation of dynamic processes that cannot be imaged at a sufficient temporal sampling rate with traditional spin trajectories. Further, use of sparsity-constrained image reconstruction supplements the tomosynthesis scan data for rapidly reconstructing artifact-free and/or quantitatively accurate images of the patient.

Faster acquisition and rapid reconstruction allows more frequent updates to the imaging information, which in turn, leads to better image quality, shorter scan durations, more accurate navigation guidance and/or simpler workflow. Additionally, faster acquisition may also allow use of less contrast agent for maintaining injected vessel image quality over the duration of the exam. Embodiments of the present systems and methods, thus, may allow for real-time imaging of transient phenomena during a plurality of clinical applications using a single system.

It may be noted that the foregoing examples, demonstrations, and process steps that may be performed by certain components of the present systems, for example, by the control mechanism 208, the DAS 212, the computing device 214, the processor 220 and/or the image reconstructor 222 may be implemented by suitable code on a processor-based system, such as a general-purpose or special-purpose computer. It may also be noted that different implementations of the present technique may perform some or all of the steps described herein in different orders or substantially concurrently, that is, in parallel.

Additionally, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code.

Although specific features of various embodiments of the present disclosure may be shown in and/or described with respect to some drawings and not in others, this is for convenience only. It is to be understood that the described features, structures, and/or characteristics may be combined and/or used interchangeably in any suitable manner in the various embodiments, for example, to construct additional assemblies and techniques.

While only certain features of the present disclosure have been illustrated and described herein, many modifications and changes will occur to those skilled in the art. It is, therefore, to be understood that the appended claims are intended to cover all such modifications and changes as fall within the true spirit of the present disclosure.

What is claimed is:

1. An imaging system, comprising:
   one or more radiation sources configured to transmit x-ray radiation towards a subject for imaging a dynamic process in a region of interest of the subject;
   one or more detectors configured to acquire projection data corresponding to the region of interest; and
   a computing device operatively coupled to one or more of the radiation sources and to the detectors, wherein the computing device is configured to:
   provide control signals for performing one or more reference scans for acquiring reference data from a plurality of angular positions around the subject;
   provide control signals for performing one or more tomosynthesis scans at limited angles using a closed acquisition trajectory for acquiring tomosynthesis data following onset of and during the dynamic process, wherein parameters that define the closed acquisition trajectory depend on a time constant of the dynamic process;
   reconstruct one or more images representative of the dynamic process using the reference data and the tomosynthesis data.

2. The system of claim 1, wherein the onset of the dynamic process corresponds to an administration of a contrast agent to the subject and/or a commencement of a motion of an interventional device.

3. The system of claim 1, wherein the one or more reference scans comprise a spin scan, a tomosynthesis scan, or a combination thereof.

4. The system of claim 1, wherein at least one of the one or more reference scans comprises a part of a continuous tomosynthesis scan performed before the onset of the dynamic process.

5. The system of claim 1, wherein the reference scan comprises an augmented tomosynthesis scan, wherein the augmented tomosynthesis scan uses additional views, denser sampling along a reference scan trajectory, a scanning trajectory having a determined tomographic angle, a spin trajectory, or combinations thereof.

6. The system of claim 1, wherein the one or more images representative of the dynamic process are generated from two or more three-dimensional volumes.

7. The system of claim 1, wherein the computing device is configured to reconstruct the one or more images based on a determined difference between the reference data and the tomosynthesis data in a projection domain.

8. The system of claim 1, wherein projection data representative of the reference scan is obtained by re-projecting a three-dimensional volume reconstructed from the reference data acquired during at least one of the reference scans.

9. The system of claim 1, wherein projection data representative of the reference scan is generated directly from the reference data acquired during at least one of the reference scans.

10. An imaging method, comprising:
    performing one or more reference scans for acquiring reference data from a plurality of angular positions around a subject;
    allowing for onset of a dynamic process in a region of interest of the subject;
    performing one or more tomosynthesis scans at limited angles using a closed acquisition trajectory for acquiring tomosynthesis data during the dynamic process, wherein parameters that define the closed acquisition trajectory depend on a time constant of the dynamic process; and
    reconstructing one or more images representative of the dynamic process using the reference data and the tomosynthesis data.

11. The method of claim 10, wherein allowing for the onset of the dynamic process comprises administration of a contrast agent to the subject and/or commencement of a motion of an interventional device.

12. The method of claim 10, wherein the one or more reference scans comprise an augmented tomosynthesis scan, wherein the augmented tomosynthesis scan uses additional views, denser sampling along a reference scan trajectory, a scanning trajectory having a determined tomographic angle, a spin trajectory, or combinations thereof.

13. The method of claim 10, wherein at least one of the one or more reference scans comprise a part of a continuous tomosynthesis scan performed before onset of the dynamic process.

14. The method of claim 10, wherein reconstructing the one or more images representative of the dynamic process are generated from two or more three-dimensional volumes corresponding to the region of interest of the subject.

15. The method of claim 10, wherein reconstructing the one or more images comprises:
   determining a difference between the reference data and the tomosynthesis data in the projection domain; and
   reconstructing the one or more images based on the determined difference.

16. The method of claim 10, further comprising obtaining projection data representative of the reference scan by re-projecting a three-dimensional volume reconstructed from the reference data acquired during at least one of the reference scans.

17. The system of claim 10, further comprising generating projection data representative of the reference scan directly from the reference data acquired during at least one of the reference scans.

18. The method of claim 10, wherein reconstructing the one or more images representative of the dynamic process comprises using sparsity-constrained image reconstruction.

19. The method of claim 10, further comprising performing functional analysis of the region of interest, guiding an interventional device, studying one or more perfusion parameters, or combinations thereof, based on the one or more images representative of the dynamic process.

20. A non-transitory computer readable medium that stores instructions executable by one or more processors to perform a method for imaging, comprising:
   performing one or more reference scans for acquiring reference data from a plurality of angular positions around a subject;
   allowing for onset of a dynamic process in a region of interest of the subject;
   performing one or more tomosynthesis scans at limited angles using a closed acquisition trajectory for acquiring tomosynthesis data during the dynamic process, wherein parameters that define the closed acquisition trajectory depend on a time constant of the dynamic process; and
   reconstructing one or more images representative of the dynamic process using the reference data and the tomosynthesis data.

* * * * *